United States Patent
Costa et al.

(10) Patent No.: US 9,792,703 B2
(45) Date of Patent: Oct. 17, 2017

(54) GENERATING A SYNTHETIC TWO-DIMENSIONAL MAMMOGRAM

(71) Applicants: Maria Jimena Costa, Nuremberg (DE); Anna Jerebko, Hausen (DE); Michael Kelm, Erlangen (DE); Olivier Pauly, München (DE); Alexey Tsymbal, München (DE)

(72) Inventors: Maria Jimena Costa, Nuremberg (DE); Anna Jerebko, Hausen (DE); Michael Kelm, Erlangen (DE); Olivier Pauly, München (DE); Alexey Tsymbal, München (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 14/792,259

(22) Filed: Jul. 6, 2015

(65) Prior Publication Data

US 2017/0011534 A1    Jan. 12, 2017

(51) Int. Cl.
*G06T 11/00* (2006.01)
*A61B 6/00* (2006.01)
*G06T 7/00* (2017.01)
*G06T 7/11* (2017.01)
*G06T 7/62* (2017.01)
*A61B 6/02* (2006.01)

(52) U.S. Cl.
CPC ............ *G06T 11/003* (2013.01); *A61B 6/025* (2013.01); *A61B 6/502* (2013.01); *G06T 7/0012* (2013.01); *G06T 7/11* (2017.01); *G06T 7/62* (2017.01); *G06T 2207/10081* (2013.01); *G06T 2207/10088* (2013.01); *G06T 2207/30068* (2013.01); *G06T 2207/30096* (2013.01)

(58) Field of Classification Search
CPC ... G06T 11/003; G06T 7/0012; G06T 7/0081; G06T 7/602; G06T 2207/30096; G06T 2207/10081; G06T 2207/10088; G06T 2207/30068; A61B 6/502
USPC .......................................... 382/131
See application file for complete search history.

(56) References Cited

U.S. PATENT DOCUMENTS

| | | | | |
|---|---|---|---|---|
| 2005/0110791 | A1* | 5/2005 | Krishnamoorthy | G06T 7/60 345/419 |
| 2008/0025592 | A1* | 1/2008 | Jerebko | A61B 6/466 382/132 |
| 2009/0202124 | A1* | 8/2009 | Matsuda | G06T 7/0012 382/128 |
| 2012/0099771 | A1* | 4/2012 | Lao | G06T 7/0012 382/131 |

(Continued)

FOREIGN PATENT DOCUMENTS

JP     2015506794    *  3/2015

*Primary Examiner* — Amandeep Saini
(74) *Attorney, Agent, or Firm* — Lempia Summerfield Katz LLC

(57) ABSTRACT

A method for generating a synthetic two-dimensional mammogram with enhanced contrast for structures of interest includes acquiring a three-dimensional digital breast tomosynthesis volume having a plurality of voxels. A three-dimensional relevance map that encodes for the voxels the relevance of the underlying structure for a diagnosis is generated. A synthetic two-dimensional mammogram is calculated based on the three-dimensional digital breast tomosynthesis volume and the three-dimensional relevance map.

15 Claims, 4 Drawing Sheets

(56) References Cited

U.S. PATENT DOCUMENTS

2015/0052471 A1\* 2/2015 Chen ..................... A61B 6/025
715/771

\* cited by examiner

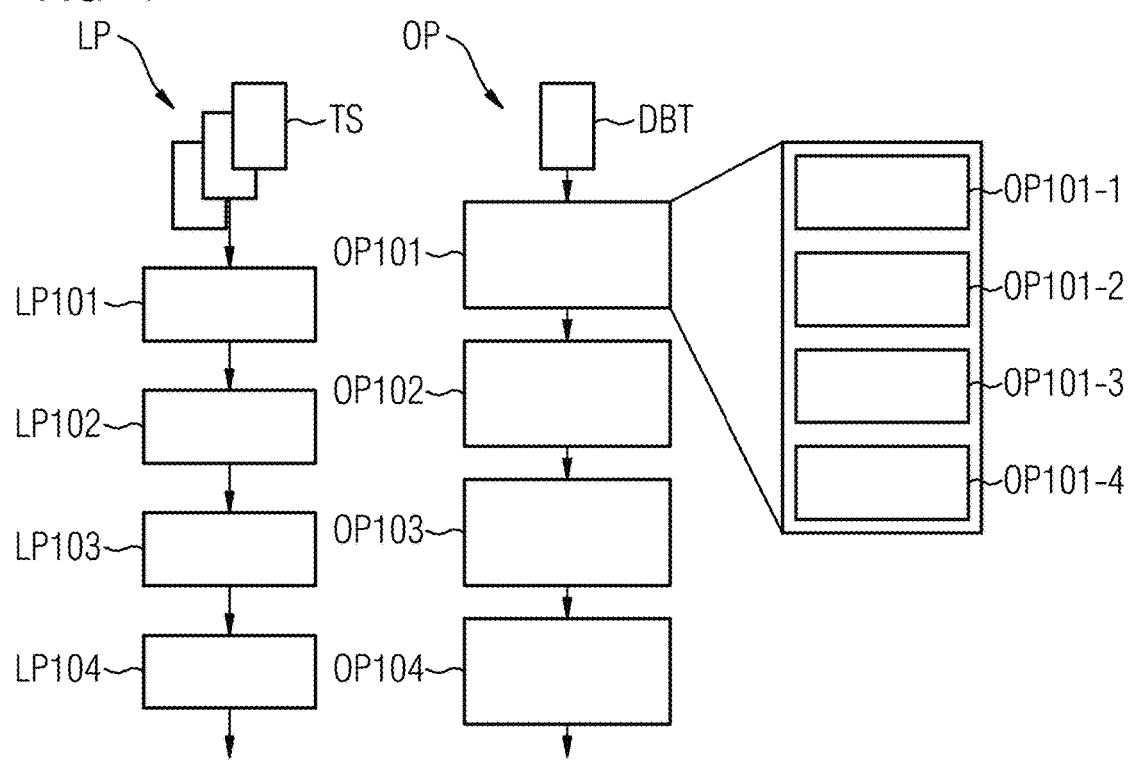
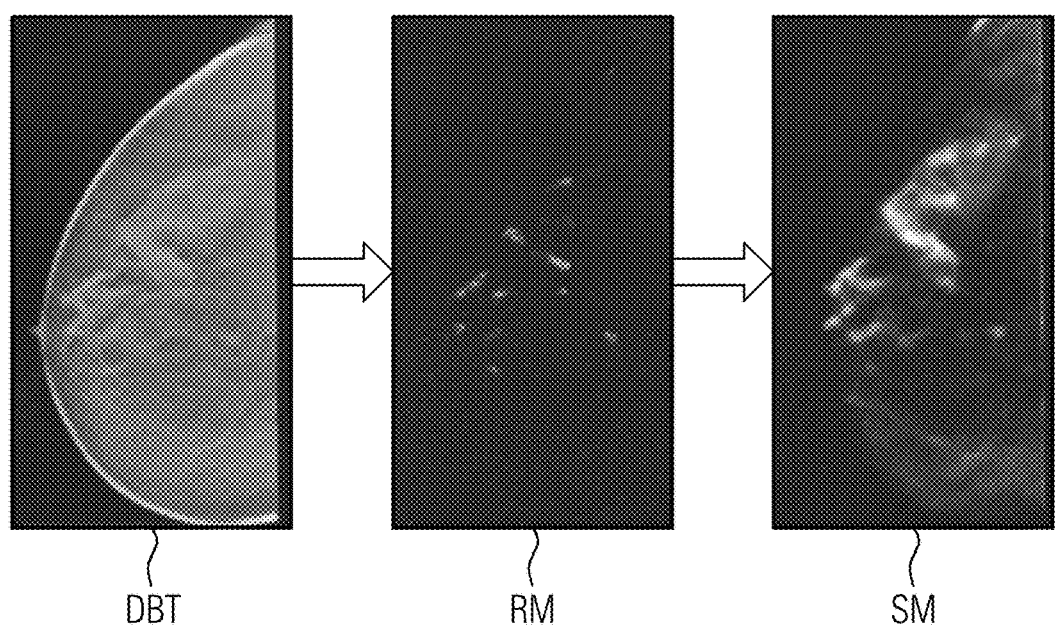

FIG 5
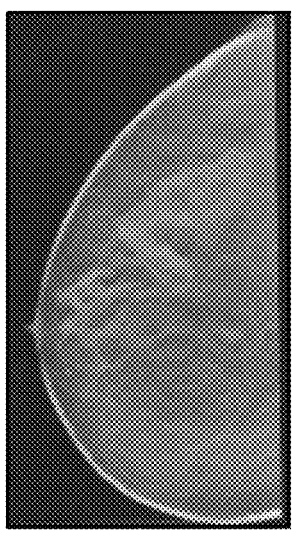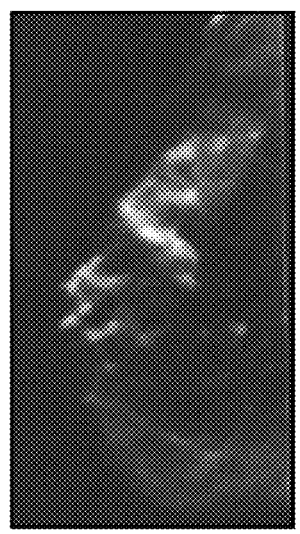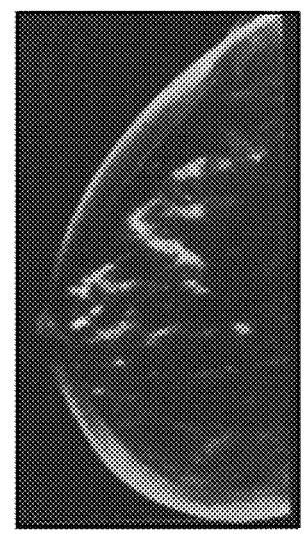

GENERATING A SYNTHETIC TWO-DIMENSIONAL MAMMOGRAM

BACKGROUND

The present embodiments relate to generating a synthetic two-dimensional mammogram with enhanced contrast for structures of interest.

In the context of breast cancer screening, digital breast tomosynthesis (DBT) is regarded as a promising modality that may replace two-dimensional (2D) mammography currently used in clinical practice. By providing three-dimensional (3D) information on the breast anatomy, DBT reduces dramatically the amount of false positive findings arising from the superposition of normal fibroglandular tissues in conventional 2D mammography.

DBT increases the workload of radiologist due to the larger number of slices to be inspected. To make diagnosis and lesion searching more efficient, a solution is to synthesize a two-dimensional mammogram from the three-dimensional DBT volume in order to guide the radiologist to the most relevant locations. The goal is to obtain an image that is comparable to conventional 2D mammography (FFDM—Full Field Digital Mammography) and may serve as fast overview of the DBT acquisition as well as for comparison with prior FFDM acquisitions. If FFDM and DBT are acquired together, a synthesized 2D mammogram may exhibit complementary information to the FFDM.

SUMMARY AND DESCRIPTION

The scope of the present invention is defined solely by the appended claims and is not affected to any degree by the statements within this summary.

The present embodiments may obviate one or more of the drawbacks or limitations in the related art. For example, contrast for suspicious structures in synthesized two-dimensional is increased.

According to a first aspect, a method for generating a synthetic two-dimensional mammogram with enhanced contrast for the structures of interest is provided. The method includes acquiring a three-dimensional digital breast tomosynthesis volume having a plurality of voxels. The method also includes generating a three-dimensional relevance map that encodes for the voxels the relevance of the underlying structure for a diagnosis, and calculating a synthetic two-dimensional mammogram based on the three-dimensional digital breast tomosynthesis volume and the three-dimensional relevance map. By the method, relevant structures in the three-dimensional digital breast tomosynthesis volume may be highlighted more precisely, and pathologic tissues may be found more exactly.

In one embodiment of the method, the three-dimensional relevance map is generated based on a predefined generating model from the acquired digital breast tomosynthesis volume. In this embodiment, the advantage that the three-dimensional relevance map may be generated automatically on each acquired digital breast tomosynthesis volume is achieved.

In a further embodiment of the method, the predefined generating model is learned by analyzing a set of three-dimensional digital breast tomosynthesis volumes. In this embodiment, the advantage that the generating model may be continuously trained by digital breast tomosynthesis volumes (e.g., annotated digital breast tomosynthesis volumes) is achieved.

In a further embodiment of the method, features are computed at the voxels of the digital breast tomosynthesis volumes to describe the local visual context. In this embodiment, the advantage that learning may be performed on recognizable features in the digital breast tomosynthesis volumes is achieved.

In a further embodiment of the method, several channels are created from the acquired digital breast tomosynthesis volume. In this embodiment, the advantage that precision of calculating a synthetic two-dimensional mammogram is increased is achieved.

In a further embodiment of the method, the channels are created based on gradient magnitudes, gradient orientations, or Laplacians. In this embodiment, the advantage that feature detection may be improved is achieved.

In a further embodiment of the method, the channels are separately analyzed to determine relevance values of the three-dimensional relevance map. In this embodiment, the advantage that more reliable relevance values are found is achieved.

In a further embodiment of the method, the generated three-dimensional relevance map is post-processed to minimize the impact of noisy predictions. In this embodiment, the advantage that quality of the relevance map is improved is achieved.

In a further embodiment of the method, post-processing is performed by using a Gaussian filtering of the generated three-dimensional relevance map. In this embodiment, the advantage that quality of the relevance map may be improved with high efficiency is achieved.

In a further embodiment of the method, a global constant weight is added to the generated three-dimensional relevance map. In this embodiment, the advantage is achieved that all calcifications, masses, and vessel structures may be captured.

In a further embodiment of the method, the synthetic two-dimensional mammogram is calculated based on raycasting in the acquired three-dimensional relevance map and the three-dimensional digital breast tomosynthesis volume. In this embodiment, the advantage that highly realistic two-dimensional mammograms may be calculated is achieved.

In a further embodiment of the method, calculating the synthetic two-dimensional mammogram is based on weighted averaging along determined rays. In this embodiment, the advantage that highly significant synthetic two-dimensional mammogram are generated is achieved.

In a further embodiment of the method, calculating the synthetic two-dimensional mammogram is based on determining a maximum weighted value found along the rays. In this embodiment also the advantage that highly significant synthetic two-dimensional mammogram are generated is achieved.

In a further embodiment of the method, the synthetic two-dimensional mammogram is displayed on a screen. In this embodiment, the advantage is achieved that the finding may be visibly inspected.

According to a second aspect, a mammographic device for generating a synthetic two-dimensional mammogram with enhanced contrast for the structures of interest is provided. The mammographic device includes an acquiring device for acquiring a three-dimensional digital breast tomosynthesis volume having a plurality of voxels. The mammographic device also includes a generating device for generating a three-dimensional relevance map that encodes for the voxels the relevance of the underlying structure for a diagnosis. The mammographic device includes a calculating device for generating a synthetic two-dimensional mammogram based on the three-dimensional digital breast tomosynthesis volume and the three-dimensional relevance map. By the mammographic device, relevant structures in the three-dimensional digital breast tomosynthesis volume may be highlighted more precisely, and pathologic tissues may be found more exactly.

According to a third aspect, a computer program product adapted to perform the method according to the first aspect, if the computer program product is run on a computer is provided. The computer program product includes a non-transitory computer-readable storage medium storing instructions executable by the computer to perform the method according to the first aspect.

BRIEF DESCRIPTION OF THE DRAWINGS

FIG. 1 shows an exemplary learning phase and an exemplary operating phase;

FIG. 2 shows exemplary images for relevance-based synthesis of a two-dimensional mammogram;

FIG. 5 shows exemplary images of relevance-based averaging and relevance-based maximum intensity projection of a two-dimensional mammogram;

DETAILED DESCRIPTION

Figure 3:
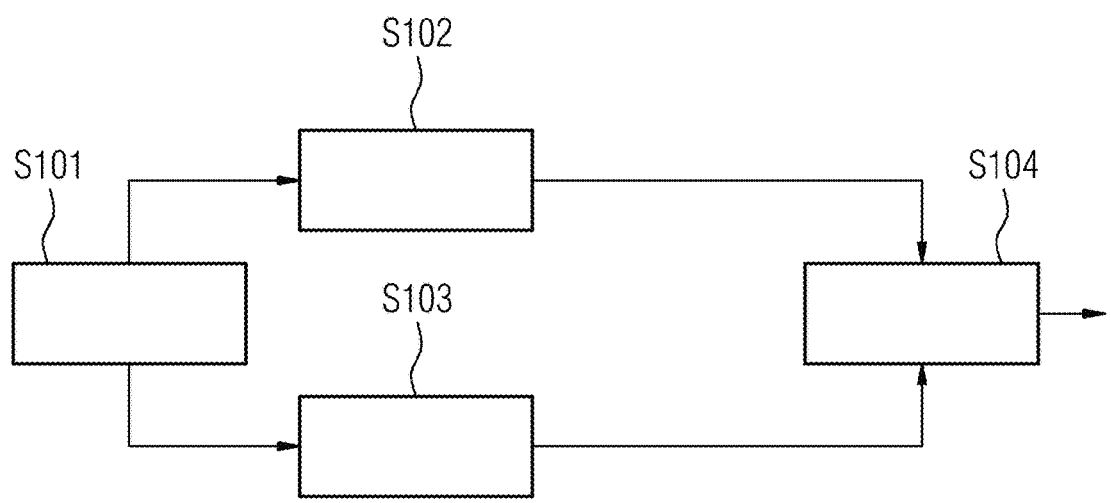
FIG. 3 shows a diagram for an exemplary relevance-based averaging.

FIG. 1 shows a learning phase LP and an operating phase OP of one embodiment of a method for generating a synthetic two-dimensional mammogram.

A learning-based approach is used for generating a synthetic 2D mammogram with enhanced contrast for the structures of interest (e.g., lesion or others interesting tissues).

The generation of a 3D relevance map encodes for each voxel the relevance of the underlying structure for breast cancer diagnosis. This 3D relevance map is then used to weight the contribution of each voxel intensity value of the 3D DBT volume during the generation process of the 2D synthetic mammogram.

A learning algorithm is trained using a database of DBT volumes in which relevant structures for diagnosis are annotated or marked. Given a newly acquired DBT volume, the trained learning algorithm is able to predict a relevance value for each voxel of the DBT volume based on the local visual context. The resulting relevance map is then used for creating the new 2D synthetic mammogram.

The learning algorithm may further evolve as new cases become available and take into account the feedback of the resident clinician. This permits to adapt the appearance of the 2D synthetic mammogram according to the imaging system conditions within the hospital. The method includes the learning phase LP and the operating phase OP.

In the learning phase LP, a model is trained using a large set of annotated or marked data to infer the relationship between the visual context of a voxel and relevance of the voxel for diagnosis. In the operating phase OP, the previously trained model is be used to infer a relevance map for a DBT volume. Afterwards, a relevance-based synthesis of 2D mammogram is performed using this relevance map.

In the learning phase, the input of the pipeline is a training set TS having a number of 3D Digital Breast Tomography volumes that are associated with expert annotations (e.g., bounding boxes around regions of interest or brushes or labels on voxels belonging to structures of interests). These manual annotations may be enriched using semi-automated segmentation approaches.

Learning Phase LP

In the pre-processing act LP101, different channels are created from the raw DBT volume using different filtering approaches (e.g., gradients magnitude, gradient orientation or second derivatives (Laplacian)). Each channel is intended to enhance specific characteristics of the visual information contained in the raw DBT volume.

In the feature extraction act LP102, features are computed at each voxel of each DBT volume to describe the local visual context in the raw volume as well as of each channel generated in the previous act LP101. Examples of features may be average intensities computed in different randomly generated sub-volumes at random offsets from the location of the voxel of interest or 3D Haar-like features. Haar-like features are 3D textural features that are derived from theory of Haar wavelet. Haar-like features are computed by locally comparing intensity averages according to certain pre-defined patterns. Haar-like features are efficiently computed using integral volumes (in 3D).

In the feature selection act LP103, only very informative features among all the features generated in the previous act are kept, by analyzing correlations of the features with the provided annotations. This may be done using, for example, maximum relevance minimum redundancy, Pearson's correlation coefficient, or other feature selection approach.

In the training act LP104, a model is trained to be able to predict a relevance value for each input voxel given a local visual context using a machine learning algorithm (e.g., characterized through a set of features). This may be performed using a classification scheme if annotations are labels such as "relevant" or "not relevant," or a regression scheme if annotations are continuous values characterizing a degree of relevance.

The output of act LP104 is a trained classifier/regressor model such as Random Forest, Support vector Machine, neural network, or any other classifier/regressor approach that is able to create the relevance map.

Operational Phase OP

The input of this pipeline is a newly acquired DBT volume as well as the model trained during the previous learning phase.

Within act OP101, the three-dimensional relevance map is generated for the acquired DBT volume using the learning model trained previously.

In the pre-processing act OP101-1, the different channels are created from the raw DBT volume.

In act OP101-2, for each voxel, the selected features are computed from the different channels generated at the previous act OP101-1.

In act OP101-3, for each voxel using the set of features from the different channels generated at the previous act OP101-2, the model is used to infer a relevance value that is stored in the three-dimensional relevance map.

In act OP101-4, this relevance map may then be post-processed to minimize the impact of noisy predictions and to provide spatial consistence. Adding a global constant weight helps to capture all calcifications, masses and vessel structures in the subsequent weighted synthesis act. In this act, the relevance map may also be combined with other relevance maps that, for example, were trained or designed to capture other tissue structures. Denoising or Gaussian filtering may be applied.

During the weighted synthesis of mammogram act OP102, information from the original DBT volume as well as the generated 3D relevance map are used to generate a 2D image containing enhanced contrast on the structures of interest or lesions.

In the post-processing act OP103, the 2D weighted mammogram may be further enhanced by using contrast-enhancement approaches such as histogram equalization or intensity windowing.

In act OP104, the resulting synthetic mammogram is displayed as well as the original DBT volume on a screen for efficient diagnosis.

FIG. 2 shows exemplary images for relevance-based synthesis of a two-dimensional mammogram SM. On the left side, the original three-dimensional DBT image is shown. In the middle, the three-dimensional relevance map RM is shown indicating for each voxel the relevance of the underlying structure for a diagnosis. On the right side, the synthetic mammogram SM obtained by weighted synthesis is shown.

FIG. 3 shows a diagram for exemplary relevance-based averaging. In relevance-based synthesis approaches in act S101, pixel location (x, y) within the original DBT is determined. In act S102, ray-casting is performed on the original DBT for each pixel location within the destination mammogram. A set of intensity values is obtained along the ray. In act S103, ray-casting is performed in the relevance map for each pixel location within destination mammogram. A set of relevance values is obtained along the ray. This permits intensity and corresponding relevance values to be sampled along the ray. In act S104, weighted averaging is used to compute the output intensity value at the pixel location (x, y) for calculating the synthetic two-dimensional mammogram.

Figure 4:
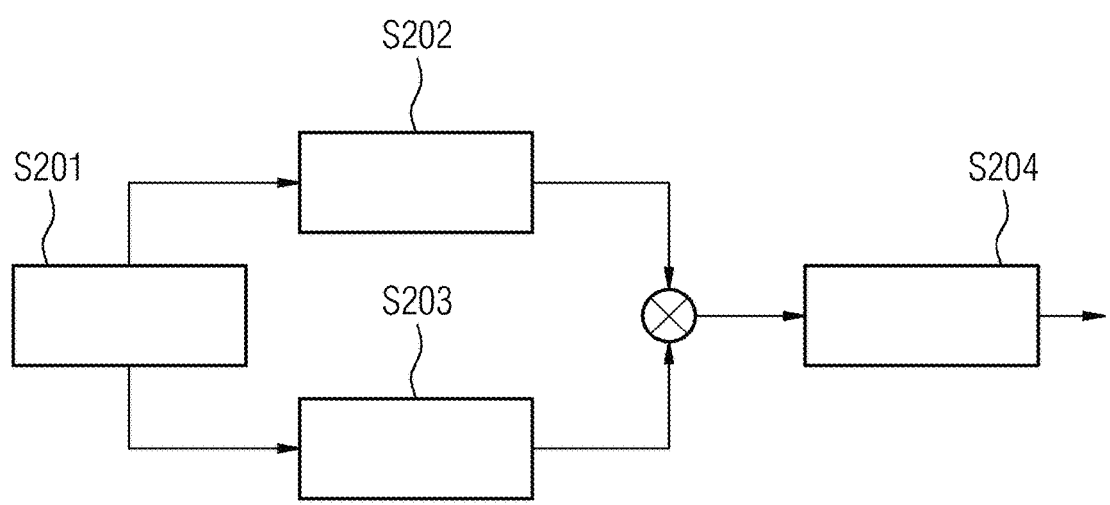
FIG. 4 shows a diagram for an exemplary relevance-based maximum intensity projection.

FIG. 4 shows a diagram for exemplary relevance-based maximum intensity projection. In act S201, pixel location (x, y) within the original DBT is determined. In act S202, ray-casting is performed on the original DBT for each pixel location within the destination mammogram. In act S203, ray-casting is performed on the relevance map for each pixel location within the destination mammogram. This permits intensity and corresponding relevance values to be sampled along the ray. In act S204, each single intensity-relevance pair is multiplied, and the maximum weighted value found along the ray is kept to compute the output intensity value at the pixel location (x, y) for calculating a synthetic two-dimensional mammogram.

FIG. 5 shows exemplary images of relevance-based averaging and relevance-based maximum intensity projection of a two-dimensional mammogram. On the left side, the original three-dimensional DBT image is shown. In the middle, the resulting image for the relevance based averaging method is shown. On the right, the resulting image for the relevance-based maximum intensity projection method for the same DBT is shown.

Figure 6:
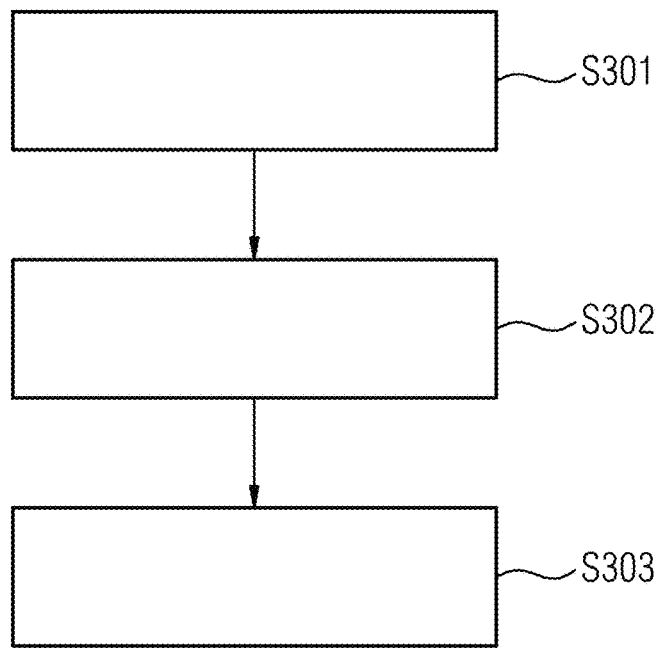
FIG. 6 shows a block diagram of one embodiment of the method.

FIG. 6 shows a block diagram of one embodiment of the method for generating a synthetic two-dimensional mammogram with enhanced contrast for the structures of interest. In act S301, a three-dimensional digital breast tomosynthesis volume having a plurality of voxels is acquired (e.g., based on computer tomography or magnetic resonance tomography). In act S302, a three-dimensional relevance map that encodes for the voxels the relevance of the underlying structure is generated for a diagnosis. The relevance map may be generated by applying a learned generating model to the acquired digital breast tomosynthesis volume (e.g., by using a computer). In act S303, a synthetic two-dimensional mammogram is calculated based on the three-dimensional digital breast tomosynthesis volume and the three-dimensional relevance map (e.g., by using the aforementioned relevance-based maximum intensity projection or relevance-based synthesis).

Figure 7:
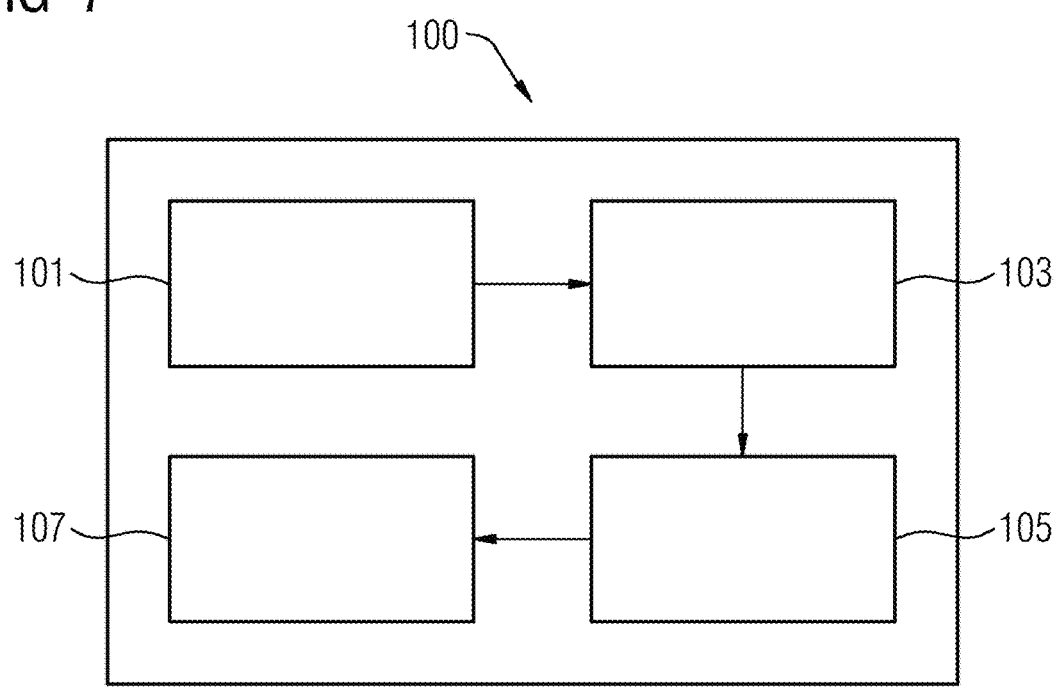
FIG. 7 shows a schematic view of one embodiment of a mammographic device.

FIG. 7 shows a schematic view of one embodiment of a mammographic device. The mammographic device 100 is configured to generate a synthetic two-dimensional mammogram with enhanced contrast for the structures of interest.

The mammographic device 100 includes an acquiring device 101 for acquiring a three-dimensional digital breast tomosynthesis volume having a plurality of voxels (e.g., a computer tomography scanner or a magnetic resonance scanner providing three-dimensional data of the tissue).

The data is transferred to a generating device 103 for generating a three-dimensional relevance map that encodes for the voxels the relevance of the underlying structure for a diagnosis. The generating device 103 may include a computer having hardware (e.g., like a processor, hard disk, memory etc.) and software that is capable for digitally analyzing the acquired three-dimensional data of the tissue.

A calculating device 105 is configured to calculate a synthetic two-dimensional mammogram based on the three-dimensional digital breast tomosynthesis volume and the three-dimensional relevance map. The calculating device 105 may also include a computer having hardware (e.g., like a processor, hard disk, memory etc.) and software that is capable for digitally calculating a synthetic two-dimensional mammogram. The calculating device 105 may be the same or a different processor than the generating device 103. In one embodiment, the generating device 103 and the calculating device 105 are formed by a computing device including one or more processors.

The calculated two-dimensional mammogram is displayed on a screen 107 for assessment of a clinician.

Within one or more of the present embodiments, a relevance map RM is used during the synthesis of the 2D synthetic mammogram SM. The relevance map RM provides information about the relevance of each structure for breast cancer diagnosis. The relevance map RM permits an enhanced 2D mammogram, in which structures are best visible using, for example, weighted ray-casting strategies, to be created. Such relevance maps RM may be automatically inferred from a new unseen DBT volume using a machine learning algorithm that models the relationship between a visual pattern and relevance of the visual pattern from a large set of DBT volumes that have been annotated.

In a first embodiment, the training phase may be described as follows. The training set may include a set of DBT volumes with bounding boxes drawn by clinicians around the region of interest. A large set of 3D Haar-like features may be extracted at each voxel location indirectly from the raw DBT volume. Feature selection is performed using Pearson's coefficient to keep a reduced number of informative features. Afterwards, a random forest may be trained to infer the probability of being relevant for diagnosis. During the operating phase, the trained random forest may be used on a newly acquired DBT volume, where the relevance of each voxel location is inferred from the extracted local features. The resulting relevance map is then used simultaneously with the raw DBT intensity values to construct the 2D synthetic mammograms using the relevance-based averaging approach described previously.

In a second embodiment, channels such as gradient magnitudes, gradient orientations, Laplacian are computed from the raw DBT volumes. A large set of 3D visual context features may be extracted at each voxel location from all channels including the raw DBT channel. Such features are defined by the computation of the average intensity computed within sub-regions of any sizes at random offsets from the considered voxel location. Afterwards, feature selection may be applied using Pearson's coefficient, and a random forest classifier is trained. The trained model is then used to infer relevance and construct 2D mammogram as in the embodiment described previously.

In a third embodiment, voxel annotations provided by clinician are continuous values that encode the relevance of the underlying structures (e.g., how much a certain structure should be visible for providing reliable diagnosis). The learning problem is formulated as a regression task where for each voxel a visual context is associated to a continuous value. Regression forests are then used to model this relationship. Given a new unseen DBT volume, the trained model may be used to generate the relevance map and the resulting synthetic mammogram.

In a fourth embodiment, an online random forest trained as described previously may be further updated to take into account clinician feedback. The structure of the random forest is changed: according to the new incoming training set, in some cases, nodes may be further split, other features may be selected, or new trees may be added. The updated random forest may then be used to infer relevance and construct 2D mammogram as in the first embodiment.

All features described with respect to method acts may be implemented by corresponding devices adapted for performing the method act. All features discussed in the description or shown in the figures may be combined in various ways in order to simultaneously realize beneficial effects. The scope of the invention is given by the claims and is neither restricted by the description nor the drawings.

The elements and features recited in the appended claims may be combined in different ways to produce new claims that likewise fall within the scope of the present invention. Thus, whereas the dependent claims appended below depend from only a single independent or dependent claim, these dependent claims may, alternatively, be made to depend, in the alternative, from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a synthetic two-dimensional mammogram with enhanced contrast for structures of interest, the method comprising:
   acquiring, with a medical scanner, a three-dimensional digital breast tomosynthesis volume having a plurality of voxels;
   generating a three-dimensional relevance map that encodes for the plurality of voxels a relevance of an underlying structure for a diagnosis; and
   calculating a synthetic two-dimensional mammogram based on the three-dimensional digital breast tomosynthesis volume and the three-dimensional relevance map,
   wherein calculating the synthetic two-dimensional mammogram is based on ray-casting in the generated three-dimensional relevance map and the acquired three-dimensional digital breast tomosynthesis volume.

2. The method of claim 1, wherein the three-dimensional relevance map is generated based on a predefined generating model from the acquired three-dimensional digital breast tomosynthesis volume.

3. The method of claim 2, wherein the predefined generating model is learned by analyzing a set of three-dimensional digital breast tomosynthesis volumes.

4. The method of claim 3, further comprising computing features at the plurality of voxels of the three-dimensional digital breast tomosynthesis volumes to describe a local visual context.

5. The method of claim 1, further comprising creating a plurality of channels from the acquired three-dimensional digital breast tomosynthesis volume.

6. The method of claim 5, wherein the plurality of channels is created based on gradient magnitudes, gradient orientations, or Laplacians.

7. The method of claim 6, further comprising determining relevance values of the three-dimensional relevance map, the determining of the relevance values comprising separately analyzing the plurality of channels.

8. The method of claim 1, further comprising post-processing the generated three-dimensional relevance map to minimize the impact of noisy predictions.

9. The method of claim 8, wherein the post-processing is performed by using a Gaussian filtering of the generated three-dimensional relevance map.

10. The method of claim 1, further comprising adding a global constant weight to the generated three-dimensional relevance map.

11. The method of claim 1, wherein calculating the synthetic two-dimensional mammogram is based on weighted averaging along determined rays.

12. The method of claim 1, wherein calculating the synthetic two-dimensional mammogram is based on determining a maximum weighted value found along rays.

13. The method of claim 1, further comprising displaying the synthetic two-dimensional mammogram on a screen.

14. A mammographic device for generating a synthetic two-dimensional mammogram with enhanced contrast for structures of interest, the mammographic device comprising:
   an imaging device configured to acquire a three-dimensional digital breast tomosynthesis volume having a plurality of voxels; and
   one or more processors configured to:
      generate a three-dimensional relevance map that encodes for the plurality of voxels a relevance of an underlying structure for a diagnosis; and
      calculate a synthetic two-dimensional mammogram based on the three-dimensional digital breast tomosynthesis volume and the three-dimensional relevance map,
   wherein the calculation of the synthetic two-dimensional mammogram is based on ray-casting in the generated three-dimensional relevance map and the acquired three-dimensional digital breast tomosynthesis volume.

15. In a non-transitory computer-readable storage medium storing instructions executable by a computer to generate a synthetic two-dimensional mammogram with enhanced contrast for structures of interest, the instructions comprising:
- acquiring a three-dimensional digital breast tomosynthesis volume having a plurality of voxels;
- generating a three-dimensional relevance map that encodes for the plurality of voxels a relevance of an underlying structure for a diagnosis; and
- calculating a synthetic two-dimensional mammogram based on the three-dimensional digital breast tomosynthesis volume and the three-dimensional relevance map,
- wherein calculating the synthetic two-dimensional mammogram is based on ray-casting in the generated three-dimensional relevance map and the acquired three-dimensional digital breast tomosynthesis volume.

\* \* \* \* \*